(12) United States Patent
Shen et al.

(10) Patent No.: US 8,244,339 B2
(45) Date of Patent: Aug. 14, 2012

(54) WIRELESS CARDIAC PULSATILITY SENSING

(75) Inventors: Xiaonan Shen, Shoreview, MN (US); Can Cinbis, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 100 days.

(21) Appl. No.: 12/852,740

(22) Filed: Aug. 9, 2010

(65) Prior Publication Data
US 2012/0035490 A1 Feb. 9, 2012

(51) Int. Cl.
*A61B 5/04* (2006.01)

(52) U.S. Cl. ........................................ 600/518

(58) Field of Classification Search .................. 600/518
See application file for complete search history.

(56) References Cited

U.S. PATENT DOCUMENTS

| | | | |
|---|---|---|---|
| 4,202,340 A | 5/1980 | Langer |
| 4,987,897 A | 1/1991 | Funke |
| 5,058,583 A | 10/1991 | Geddes et al. |
| 5,409,009 A | 4/1995 | Olson |
| 5,469,859 A | 11/1995 | Tsoglin |
| 5,507,785 A | 4/1996 | Deno |
| 5,511,553 A | 4/1996 | Segalowitz |
| 5,713,935 A | 2/1998 | Prutchi |
| 5,824,029 A | 10/1998 | Weijand |
| 6,360,123 B1 | 3/2002 | Kimchi |
| 6,449,504 B1 * | 9/2002 | Conley et al. ................. 600/523 |
| 7,162,288 B2 | 1/2007 | Nordstrom |
| 2005/0090753 A1 | 4/2005 | Goor |
| 2006/0036288 A1 | 2/2006 | Bocek et al. |
| 2006/0247735 A1 | 11/2006 | Hornert |
| 2007/0054871 A1 | 3/2007 | Pastore |
| 2007/0273504 A1 | 11/2007 | Tran |
| 2007/0299477 A1 | 12/2007 | Kleckner et al. |
| 2008/0058669 A1 | 3/2008 | Kroll |
| 2008/0281367 A1 | 11/2008 | Zhang |
| 2009/0240132 A1 | 9/2009 | Friedman |
| 2009/0240133 A1 | 9/2009 | Friedman |

FOREIGN PATENT DOCUMENTS

| WO | 01/13792 A1 | 3/2001 |
|---|---|---|
| WO | 02/20086 A1 | 3/2002 |

OTHER PUBLICATIONS

P0037068.WOU2 (PCT/US2011/047037) PCT Notification of Transmittal of the International Search Report and the Written Opinion of the International Searching Authority, Mailed Nov. 11, 2011, 14 pages.
Tacker et al., "Perivascular Impedance Sensors for In Vivo Chronic Blood Pressure Measurement: Detection Systems for Automatic Defibrillators, Cardioverters and Blood Pressure Controllers", Proceedings of the Annual Conference on Engineering in Medicine and Biology, The Conference Committee, Baltimore, US, Jan. 1984, p. 20, ISSN: 0589-1019.

* cited by examiner

*Primary Examiner* — George Manuel
(74) *Attorney, Agent, or Firm* — Michael C. Soldner; Evans M. Mburu; Stephen W. Bauer

(57) ABSTRACT

An implantable medical device system and associated method monitor changes in transimpedance in a body tissue due to changes in cardiac pulsatility. A first dipole is used to deliver a non-stimulating electrical current. The first dipole includes a first electrode and a second electrode adapted to be deployed along a first body location. A second dipole is used to measure a voltage resulting from the non-stimulating electrical current being conducted through a portion of a patient's body. The second dipole includes a third electrode and a fourth electrode different than the first electrode and the second electrode and adapted to be deployed along a second body location spaced apart from the first body location.

19 Claims, 6 Drawing Sheets

US 8,244,339 B2

WIRELESS CARDIAC PULSATILITY SENSING

TECHNICAL FIELD

The disclosure relates generally to implantable medical devices and, in particular, to a method and apparatus for monitoring cardiac pulsatility.

BACKGROUND

Implantable cardioverter defibrillators (ICDs) typically sense intracardiac EGM signals for detecting arrhythmias. Ventricular tachycardia (VT) and fibrillation (VF) are detected by analyzing cardiac intervals, sometimes in conjunction with EGM signal morphology analysis. When VT or VF is detected, the heart may be cardioverted or defibrillated using one or more high voltage shocks. A shock may be delivered immediately when the detected arrhythmia is considered to be a potentially lethal arrhythmia. A shock may be delivered after less aggressive pacing therapies are attempted first and are unsuccessful in terminating VT.

A shock is painful to the patient and uses considerable battery energy. The avoidance of unnecessary shocks is important in preventing undue pain to the patient and to conserve battery longevity of the implanted device. An unnecessary shock may be delivered, for example, when VT or VF is falsely detected due to oversensing of non-cardiac signals, T-wave oversensing, or when a supraventricular tachycardia (SVT) is falsely detected as VT or VF. A need remains, therefore, for reducing the number of unnecessary shocks delivered by ICDs.

DETAILED DESCRIPTION

Figure 1:
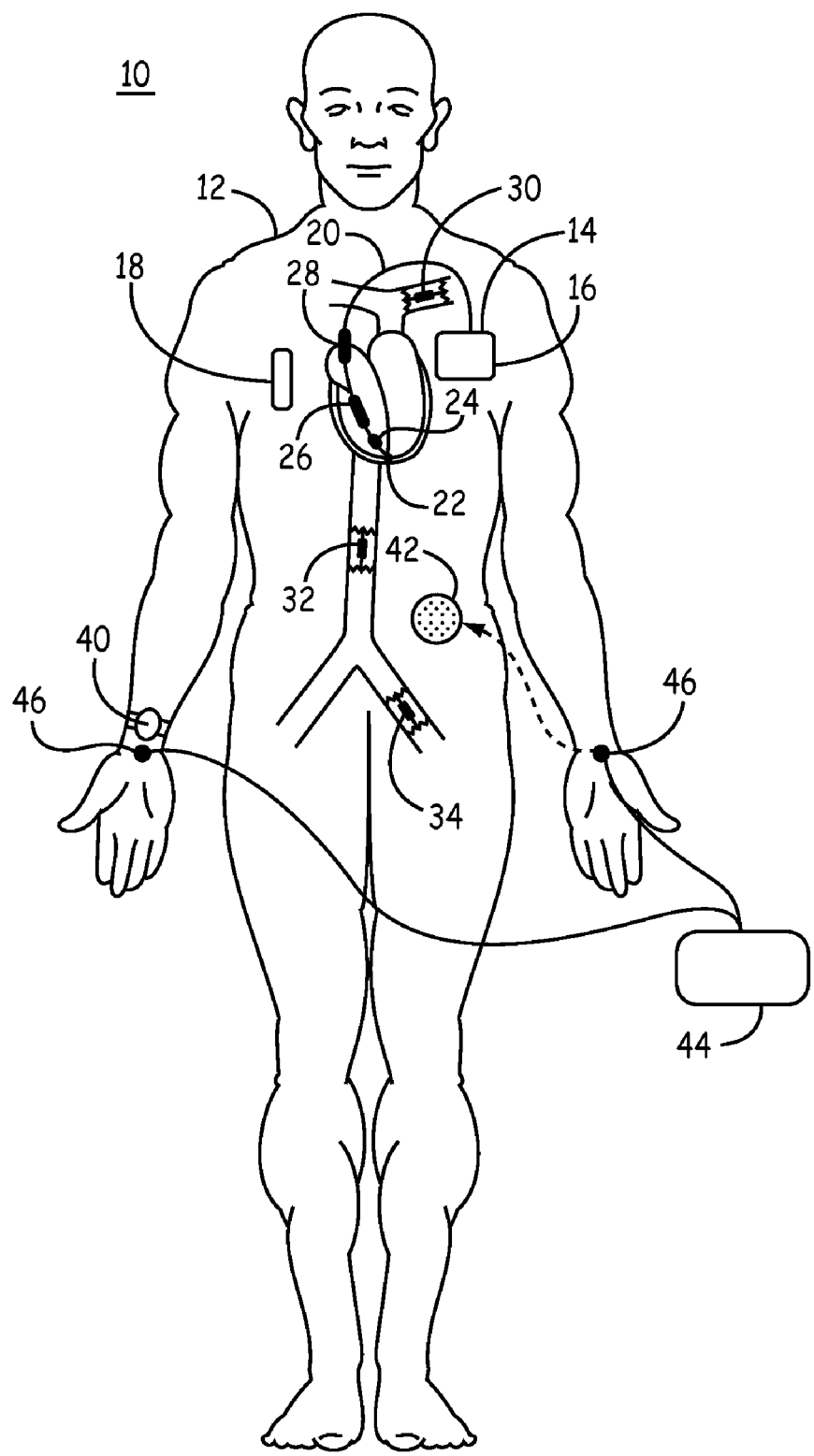
FIG. 1 is a schematic diagram of a medical device system in which monitoring methods disclosed herein may be implemented.

In the following description, references are made to illustrative embodiments. It is understood that other embodiments may be utilized without departing from the scope of the disclosure. In some instances, for purposes of clarity, similar reference numbers may be used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

FIG. 1 is a schematic diagram of a medical device system 10 in which monitoring methods disclosed herein may be usefully practiced. As will be described in detail, a system and method for wirelessly monitoring cardiac pulsatility measures a signal correlated to transimpedance using a first dipole located along a first device and a second dipole located along a second device that is not electrically wired or mechanically coupled to the first device. Numerous dipole pair configurations are possible that variously employ implanted lead-based electrodes, implanted leadless electrodes incorporated along the housing of an implantable medical device, and/or surface (skin) electrodes located externally on the patients body.

To illustrate various possible configurations, a patient 12 is shown having an implantable medical device (IMD) 14 coupled to a transvenous intracardiac lead 20, a leadless IMD 18, transvenously depoloyed IMDs 30, 32, and 34, an externally-worn device 40, an external patch electrode 42, and one or more external limb electrodes, referred to collectively by reference numeral 46, coupled to an external medical device 44. It is to be understood that a patient may be provided with any of these devices and electrodes but not necessarily all of the devices and electrodes shown. The devices and electrodes shown in FIG. 1 are for illustrative purposes only and the actual components included in a particular medical device system will vary between embodiments depending on the particular monitoring application needed for a given patient. The methods described herein are not limited to any particular combination of medical devices and electrodes so long as an electrode configuration is available allowing two distinct dipoles, located at spaced apart body locations, to be used to measure transimpedance.

"Transimpedance" as used herein refers to the ratio of a voltage signal measured at a body location by a measurement dipole to a drive current signal applied to a transmission dipole located at a body location spaced apart from the measurement dipole. The measurement dipole and the transmission dipole are distinct in that no common electrode is shared between the two dipoles, in contrast to, for example, a tripolar impedance measurement system in which electrode pairs share a common ground. The transimpedance is measured through the intervening volume of conductive body tissue (or fluid) located between the two dipoles and is therefore a wireless measurement through the body tissue since the measurement dipole is not coupled to a common ground with the transmission dipole. Changes in transimpedance, and resulting changes in voltage at a measurement dipole given a known drive current signal, reflect resistivity and volume changes in the tissue volume of interest.

Transimpedance monitoring using separate distinct dipoles deployed without being electrically wired or mechanically coupled to a common device can be particularly useful for monitoring changes in deep tissue. Separate and distinct dipoles allow dipole placement in a specifically selected tissue volume, which may be highly localized. Use of bipolar or tripolar impedance measurements will always include the polarization effects at the drive current electrode(s). With no common ground shared between a transmission dipole and a measurement dipole, the measured signal at the measurement dipole will be tightly related to the drive signal, providing a signal highly correlated to the changes in impedance in the intervening tissue with greater signal content than impedance signals measured using a bipolar or tripolar arrangement wherein transmission and measurement electrodes are electrically tied to a common device.

Numerous possible transimpedance monitoring configurations are available in the schematic diagram of FIG. 1. The IMD 14 includes a housing electrode 16 which may be used in conjunction with any of the tip electrode 22, ring electrode 24, right ventricular (RV) coil electrode 26 or superior vena cava (SVC) coil electrode 28 to form a dipole used in measuring transimpedance. The dipole may be a transmission dipole that injects a high-frequency current signal that does not stimulate excitable body tissue. Alternatively the dipole may be a measurement dipole that is used to measure the voltage that results from a drive current signal being conducted through the conductive fluids present in body tissue. For example, a dipole selected using at least one of the electrodes carried by lead 20 may be used in combination with a dipole provided on one of the transvenous devices 30, 32 or 34.

Transvenous devices 30, 32, and 34 are shown positioned in the left pulmonary artery, abdominal aorta, and femoral artery, respectively, as examples of possible implant locations. Transvenous devices 30, 32 and 34 may be embodied as dedicated transimpedance monitoring devices provided with a pair of exposed electrodes for use in transmitting a non-stimulating drive current signal or for measuring a voltage signal conducted through body tissue resulting from a drive current signal injected by a dipole located at a different body location.

The transvenous devices 30, 32, and 34 may additionally include other monitoring functionality and may include a pressure transducer, an optical transducer, a flow transducer, an acoustical transducer or other signal transducer used to sense a physiological signal for monitoring the patient. For example, any of the transvenous devices 30, 32, and 34 may be provided as a wireless blood pressure sensor, blood oxygen sensor, heart sound sensor, blood flow sensor, or the like. The transvenous devices 30, 32 and 34 may include an electrode pair used for sensing ECG signals in addition to being used as a dipole for performing transimpedance measurements.

In one embodiment, a transvenous sensor 30, 32 or 34 is provided with a physiological sensor for monitoring a physiological signal other than impedance and a pair of electrodes used for transmitting a data signal to another medical device, such as IMD 12, via a body bus communication. Reference is made to U.S. Pat. No. 4,987,897 (Funke), which generally describes the use of a body bus communication between medical devices, hereby incorporated herein by reference in its entirety. As will be described further herein, a data signal transmitted from an implanted sensing device via a wireless communication may be used as a drive signal for measuring a transimpedance signal at receiving dipole of another implanted device.

In another transimpedance monitoring configuration, an extravascular IMD 18 may be provided with an electrode pair for use as a transmitting or a measurement dipole. IMD 18 may include electrodes for use in monitoring ECG signals of the patient which may additionally serve as a dipole for transimpedance measurements. IMD 18 could be used in combination with any of the lead-based electrodes 22, 24, 26 or 28 or housing electrode 16 associated with IMD 14 selected in a dipole pair or with a dipole available on any of the transvenous IMDs 30, 32, or 34.

In addition to implantable electrodes, external electrodes may be used in as one dipole for measuring transimpedance. For example, wearable device 40 may be provided with a pair of electrodes in contact with the patient's skin, e.g., in a wearable "wrist-watch" type of device, that may be used as a dipole for either transmitting a drive current or for measuring a voltage signal through body tissue resulting from a drive current injected by a different dipole at another body location. A wearable wrist-watch type of device may be provided with one electrode in contact with the skin of the wrist and the other contacted by the digits of the opposing hand. Such a dipole can be used to measure a voltage signal corresponding to a relatively global transimpedance in response to an injected drive signal at another body location.

Alternatively, a surface electrode in the form of a patch electrode 42 may be used with a second surface patch electrode (not shown) or a limb contact electrode 46 to form a dipole pair for use in transimpedance measurements. Depending on the positioning of external surface electrodes, a patient may be instructed to hold a limb contact electrode 46 in proximity to a surface patch electrode 42 to form a dipole pair in close proximity to each other.

In some embodiments, both the transmitting and the measurement dipole pairs may be configured as external electrodes only with a transimpedance measurement signal received by an external monitoring device 44 for analysis and use in a diagnostic algorithm. Alternatively the external device 44 may transmit the transimpedance signal to an implanted device, such as IMD 14, for use in detecting physiological conditions or events and in controlling a device-delivered therapy. A transimpedance signal measured using an external dipole configuration may also be transmitted to an internal device via a body bus communication or radio-frequency communication.

In other embodiments, an external dipole may provide a drive signal for injecting current that is conducted through a volume of body tissue and the resulting voltage is measured at an implanted dipole pair using any of the implanted devices shown in FIG. 1. In this case, the power source used to generate the drive current is an external power source and not an additional drain on the battery of an implanted device. After transimpedance monitoring is completed, external electrodes may be removed and information about a patient's condition learned from the transimpedance signal data may be used in programming therapies delivered by an implanted device.

The various devices or electrodes shown in FIG. 1 are positioned at body locations such that two distinct dipole pairs are positioned at spaced apart locations with a volume of body tissue of interest for transimpedance monitoring positioned between the dipoles. The dipoles may be positioned close together to obtain a relatively localized measurement of transimpedance or separated by a greater distance to obtain a more global measurement of transimpedance. For example, two dipoles positioned relatively close together can be positioned on either side and along a small artery to monitor pulse profile of the artery. A larger spacing between dipoles can be used to obtain relatively more global measurements, e.g. relating to respiration monitoring. The spacing between dipoles may range from a few millimeters to several feet depending on the monitoring application.

In a general sense, a voltage signal strength at the measurement dipole will relate positively to the transmitted drive current and intra-dipole spacing (electrode separation within each dipole), and negatively relates to inter-dipole spacing (distance between the transmitting dipole and the measurement dipole). Local pulsatility monitoring can be conducted with dipoles having close intra-dipole and inter-dipole spacing. In this configuration, the intra-dipole spacings can be in the range of a few millimeters to tens of millimeters, e.g. approximate 2 mm to approximately 1 cm. The inter-dipole spacing can be in the range of a few millimeters to a few centimeters, e.g. in the range of approximately 3 mm to approximately 10 centimeters. The dipoles can be aligned with each other to maintain an adequate drive current in the micro-ampere to few milliamperes range.

For more global pulsatility measurements, e.g. through the patient's torso, larger inter-dipole spacing is needed. In order to maintain adequate signal strength for relatively more global measurements, a relatively stronger drive current and/or a larger intra-dipole spacing is needed. If the drive current signal is in the range of a few milliamperes, an intra-dipole spacing ranging from approximately 2 centimeters to approximately 100 centimeters is expected to provide adequate signal strength, depending in part on the electrical properties of the intervening tissue, for obtaining a global pulsatility measurement.

Each electrode on each dipole is provided with a surface area large enough to ensure a low current density level during drive current transmission for stimulation avoidance. For intermittent injection of an alternating drive current having an amplitude in the milli-ampere range and a frequency in the kilohertz range, an electrode surface are of a few square millimeters will be sufficient, e.g. approximately 10 square millimeters or more. The electrode surface area needed to prevent tissue stimulation will vary between embodiments depending on surrounding tissue type and other factors.

The various ranges and distances described in the foregoing examples relating to electrode size and spacing between and within dipoles are intended to be illustrative, without limitation. Practice of the methods described herein are not limited to any particular range of inter-dipole spacing, intra-dipole spacing and electrode size as these specifications will be selected as appropriate for a particular monitoring application.

In one embodiment, the dipoles are positioned to include a portion of the heart therebetween to allow transimpedance measurements of cardiac tissue to be measured. In other embodiments, the dipoles may be positioned within a blood vessel or heart chamber such that transimpedance measurements of a volume of blood between the dipoles can be monitored. In still other embodiments, a volume of muscle tissue, nerve tissue (including brain or spinal cord), or other organs may be monitored.

Figure 2:
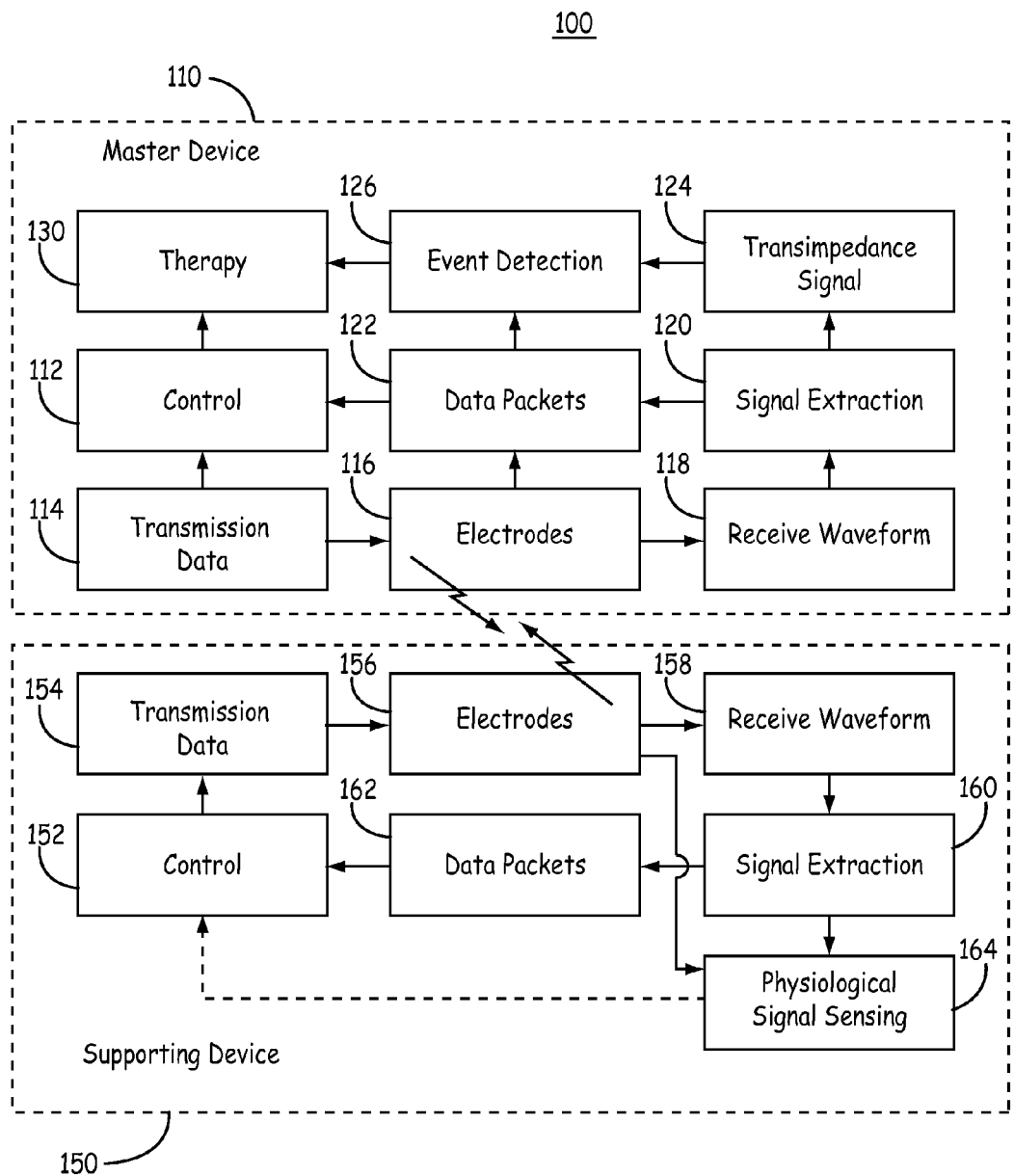
FIG. 2 is a functional block diagram of one embodiment of a medical device system providing wireless transimpedance monitoring.

FIG. 2 is a functional block diagram of one embodiment of a medical device system providing wireless transimpedance monitoring. The system 100 includes two medical devices 110 and 150 capable of wireless bidirectional communication via a body bus. Each device 110 and 150 is provided with at least one pair of electrodes 116 and 156, respectively, used for transmitting and receiving communication data. The electrodes are also used as a dipole for wirelessly monitoring transimpedance in a portion of a patient's body.

In some embodiments, one device 110 functions as a master device and the other device 150 functions as a supporting device that responds to requests for data from the master device 110. In other embodiments, both devices 110 and 150 may make a data request with the other device responding to such requests. For illustrative purposes, the following functional description of system 100 describes the device 110 functioning as a master device capable of requesting data from the supporting device 150 with the supporting device 150 functioning as a physiological monitor for acquiring data about a patient condition.

Master device 110 includes a control module 110, which may be a microprocessor and associated memory, a state machine, or other appropriate circuitry for performing operations and algorithms that control the various functions of device 110. Control 112 may issue a data request by generating transmission data 114 that specifies the type of data being requested from supporting device 150 and any transmission instructions. This transmission data is transmitted from the master device 110 to the supporting device 110 via a body bus communication using electrodes 116.

Supporting device 150 receives the transmission data via electrodes 156. The receive waveform block 158 is coupled to the electrodes for receiving the analog transmission data and may amplify and filter the analog waveform and perform analog-to-digital conversion of the waveform. The received waveform undergoes signal extraction at block 160 to determine what data is being requested and any other data transmission instructions.

If additional physiological signal data is required that has not already been acquired by the supporting device, physiological signals may be sensed by sensing block 164. The electrodes 156 may be used as measurement electrodes for monitoring a transimpedance signal. In some embodiments, the electrodes 156 may be used for sensing EGM, ECG, EEG or EMG signals when physiological sensing is required. Additionally or alternatively, other physiological signal sensors may be included in device 150 for sensing pressure, flow, oxygen saturation, or any of the other types of physiological signals listed herein.

Data packets are assembled at block 162 for signal transmission back to the master device 110 according to the instructions extracted from the received transmission request. The data packets may include raw physiological signal data or processed signal data. The control module 152 receives the data packets and generates the transmission data 154 to be sent back to master device 110 in accordance with the data request instructions. The transmission data is transmitted via electrodes 156 through a body bus communication pathway to the master device 110.

The master and supporting devices may be configured to monitor a transimpedance signal in a variety of ways. In one embodiment, the master device injects a drive current signal via electrodes 116. The supporting device measures the resulting voltage using electrodes 156 and the analog voltage signal is received at block 158 for amplification and filtering. The analog voltage signal may be used directly or further analyzed using the known current drive signal to compute a transimpedance signal. The voltage signal (or a computed transimpedance signal) may be analyzed by signal extraction block 160 and processed transimpedance data may be assembled in data packets at block 162 for transmission back to the master device 110.

In another embodiment, master device 110 transmits a request to supporting device 150 for a drive current signal to enable master device 100 to perform transimpedance measurements. In this case, the supporting device 150 responds to the request by injecting a drive current signal using electrodes 156. A resulting voltage signal measured at electrodes 116 by the master device 110 is received at block 118 and processed by signal extraction block 120 to determine transimpedance information at block 124.

Alternatively, the supporting device 150 may be transmitting a data signal relating to a physiological signal monitored by supporting device 150, such as a pressure, flow, or other signal. The data signal is transmitted via electrodes 156 to master device 110, on a continuous or periodic basis or upon request from master device 110. The data signal being transmitted may be a raw physiological signal or processed physiological data. The transmitted data signal can additionally serve as the injected drive current signal for measuring transimpedance. As such, whenever master device 110 receives a data signal waveform from supporting device 150, master device 110 may additionally measure the transimpedance signal by measuring the voltage signal at electrodes 116 and computing the transimpedance. A communication data packet can include information on the drive current signal injected by the supporting device to enable computation of the transimpedance signal from the voltage signal.

In this way, data transmission from supporting device 150 provides physiological data needed by master device 110 for detecting events and/or making therapy delivery decisions and provides a drive signal for monitoring transimpedance by master device 110. Supporting device may be a wireless physiological sensor implanted intra-or extravascularly, remotely from the master device 110. The master device 110 may be an ICD, pacemaker, drug pump or other therapy delivery device.

A receive waveform block 118 in master device 110 may provide analog amplification and filtering and analog-to-digital conversion of a received signal. Signal extraction block 120 extracts physiological signal information from the digitized signal. Data packets are assembled at block 122 from the extracted signal for use by control module 112. These data packets include the physiological data acquired by the supporting device 150 and may include other device-or communication-related data.

Transimpedance signal block 124 determines the transimpedance signal from the received waveform. When a data communication signal is used as the drive signal for performing transimpedance measurements, the transimpedance signal block may include a number of processing steps for extracting signal variation caused by pulsatile changes in the resistivity and conductance of the body tissue from the data communication carrier signal.

Numerous methods may be used for extracting the desired transimpedance-related signal. In one embodiment, a phase locked loop (PLL) or frequency locked loop (FLL) can be employed to lock into a carrier frequency of the data communication transmission signal. A multiplier block (not shown explicitly) multiplies the incoming signal with a reference signal and a 90 degree phase-shifted reference signal from the PLL or FLL (fixed amplitude). This process will shift the transimpedance-related information to baseband providing in-phase and quadrature components. A low-pass filter will expose the physiologic variations on the data transmission transimpedance signal. A magnitude operation using in-phase and quadrature components will provide a transimpedance related magnitude signal. An arctangent of division of quadrature to in-phase component operation will give a phase signal.

In an alternative technique, a narrow-band filter centered around the data transmission carrier frequency can provide a signal that when amplified, rectified with a diode, and RC low-pass filtered will provide a transimpedance-related magnitude signal.

Event detection block 126 is a processing block which may use the physiological data packets 122 from supporting device 150, transimpedance data from block 124, and any other physiological data acquired by the master device 110 to detect physiological conditions or events. Therapy module 130 delivers a therapy as needed in response to event detection block 126 and under the control of control module 112.

Figure 3:
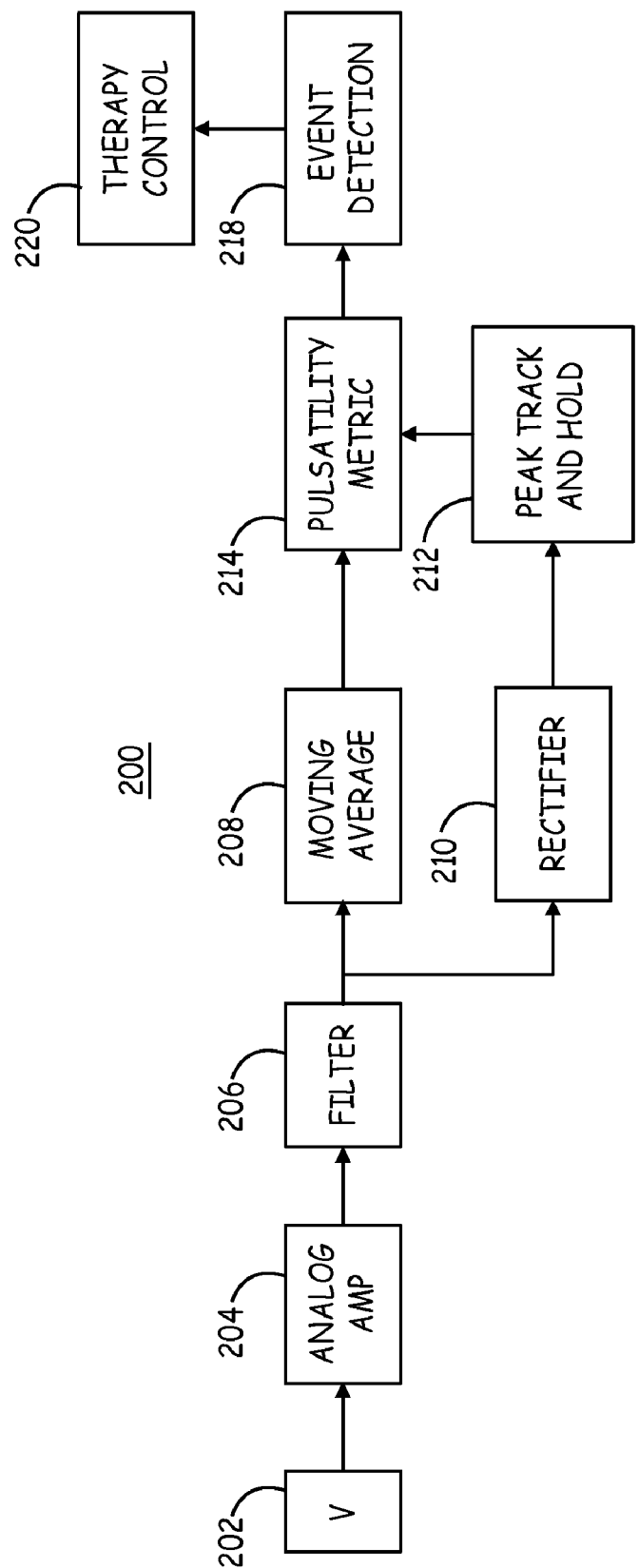
FIG. 3 is a functional block diagram of the processing of a transimpedance signal for use in determining a pulsatility metric.

FIG. 3 is a functional block diagram 200 of the processing of a transimpedance signal for use in determining a pulsatility metric. One purpose of monitoring transimpedance is for verifying a pulsatile signal as evidence of tissue perfusion or heart function. At block 202, a voltage signal resulting from an injected drive current signal at a first dipole is measured using a second dipole spaced apart from the first dipole. The voltage signal may be amplified by an analog amplifier at block 204 and then filtered at block 206. Filter 206 may be a low pass or bandpass filter having a pass band corresponding to a cardiac pulsatility frequency range, e.g. a pass band of approximately 0.5 Hz to approximately 10 Hz, though other narrower or wider ranges may be used. A lower cut off frequency may be selected to remove or reduce respiration noise from the impedance signal.

In some embodiments, the voltage signal is used directly without computing transimpedance, e.g. when the current drive signal is a fixed signal, e.g. a 100 KHz sine wave. In other embodiments, transimpedance is computed from the measured voltage signal and the known drive signal. In particular, when the drive signal is a time varying signal such as a body bus data communication signal, the known carrier signal information can be used in a signal extraction process as described above for obtaining a pulsatile voltage signal correlated to pulsatile changes in transimpedance in the tissue.

The filtered signal is provided as input to a moving average block 208 which computes a moving average of the filtered signal over a selected time window. For example, the moving average time window may be in the range of approximately 2 seconds to approximately one minute or more. In one embodiment, a moving average of the voltage signal is computed over approximately 4 seconds. The moving average time window is selected to be long enough to allow a change in pulsatility associated with a monitored condition or event of interest to occur within the time window.

The filtered signal output of block 206 is received as input to a rectifier block 210. Rectifier 210 provides a rectified signal to a peak track and hold block 212, which tracks and holds a peak amplitude of the rectified signal. The peak track and hold block 212 holds the value of a detected peak amplitude for a selected hold interval. The selected hold interval is a portion of the moving average window to allow a change in pulsatility relative to the moving average to be detected with a desired time resolution. The desired time resolution will depend on the type of condition being monitored. For example, if pulsatility is being monitored for use in verifying a need for delivering a cardiac shock from an ICD, the change in pulsatility due to the onset of fibrillation will likely occur within a short time interval of one second or less. For this type of application, the peak hold interval may be approximately 1 to 2 seconds and the moving average window may be approximately 2 to 4 seconds, for example. In other applications where a change in pulsatility occurs more gradually over a longer period of time, the moving average window and the peak hold window may be selected to be appropriately longer intervals.

At processing block 214, a pulsatility metric is computed using the moving average signal from block 208 and the peak amplitude signal from peak track and hold block 212. For example, a ratio of the peak amplitude to the moving average may be computed and expressed as a percentage. This percentage can be used as a pulsatility metric in that it is a measure of the detected peak amplitudes as a percentage of the moving average. As the blood pressure pulse in a tissue declines or as the heart begins to beat less effectively, e.g. as in fibrillation, the percentage pulsatility will decline.

The output of block 214 is provided as input to a event detection block 218 for use in an algorithm, which optionally utilizes other physiological signals in combination with the pulsatility metric, for detecting or confirming a physiological event or condition. The output of event detection 218 can then be used by a therapy control block 220 in making therapy delivery decisions. A decision to start, stop or adjust a therapy may be made based, at least in part, on the pulsatility metric. It is recognized that the blocks in FIG. 3 may be arranged in a different order than shown and still operate to obtain a pulsatility metric and that other methods may be used in obtaining a metric of pulsatility using a time-varying transimpedance signal measured using a pair of distinct and separate dipoles.

Figure 4A:
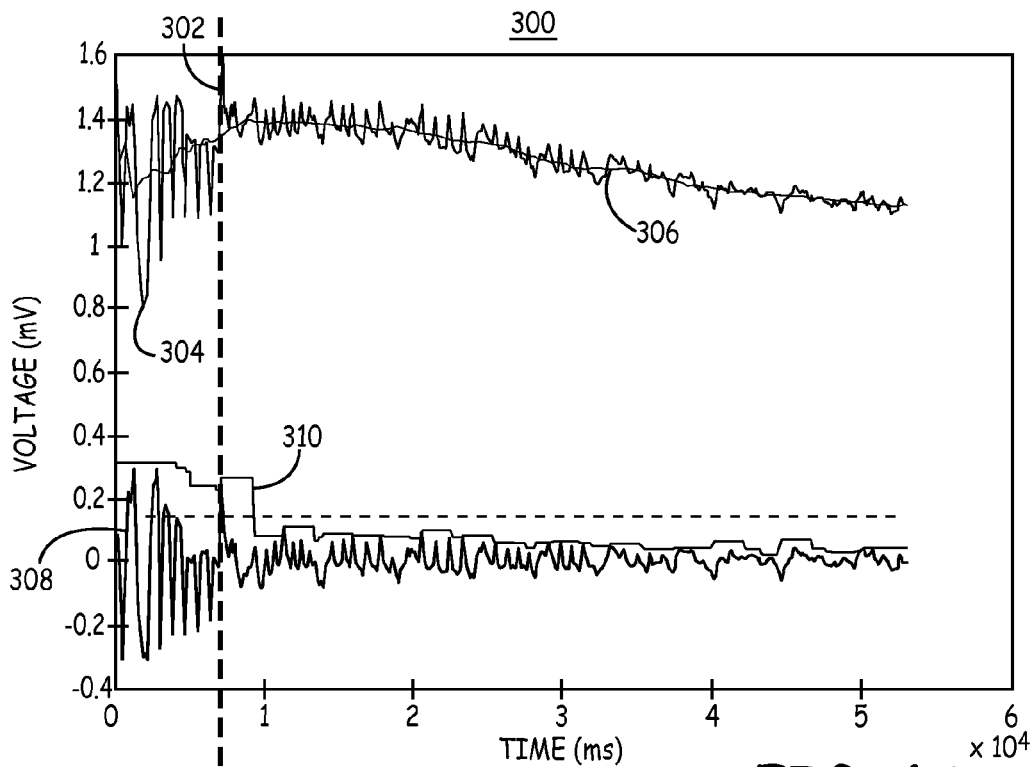
FIG. 4A is a time-based plot of a voltage signal used for monitoring tissue pulsatility.

FIG. 4A is a time-based plot 300 of a voltage signal 304. Voltage signal 304 was measured using a dipole pair configuration including a first dipole for injecting a current signal and a second dipole, distinct from the first dipole, for measuring the resulting voltage signal. The voltage signal 304 is measured before and after inducing fibrillation at 302 in an experimental subject. The voltage signal 304 varies with cardiac pulsatility and with respiration.

In this example, the voltage signal is measured using a dipole formed by an RV coil electrode positioned in the subject's right ventricle and the housing electrode of an ICD implanted in the left pectoral region. The drive current was injected using a dipole formed by an electrode pair carried by a catheter positioned in the right pulmonary artery and not electrically wired to the ICD. This positioning of the dipoles results in a large volume of cardiac tissue between the two dipoles such that a change in the voltage signal will be highly correlated to a change in cardiac pulsatility.

A moving average 306 of the voltage signal 304 is computed over a four-second moving window. Voltage signal peaks (positive or negative peaks) are detected from a cardiac filtered voltage signal 308. The absolute value of the voltage signal peaks are used to produce a peak voltage signal 310.

Figure 4B:
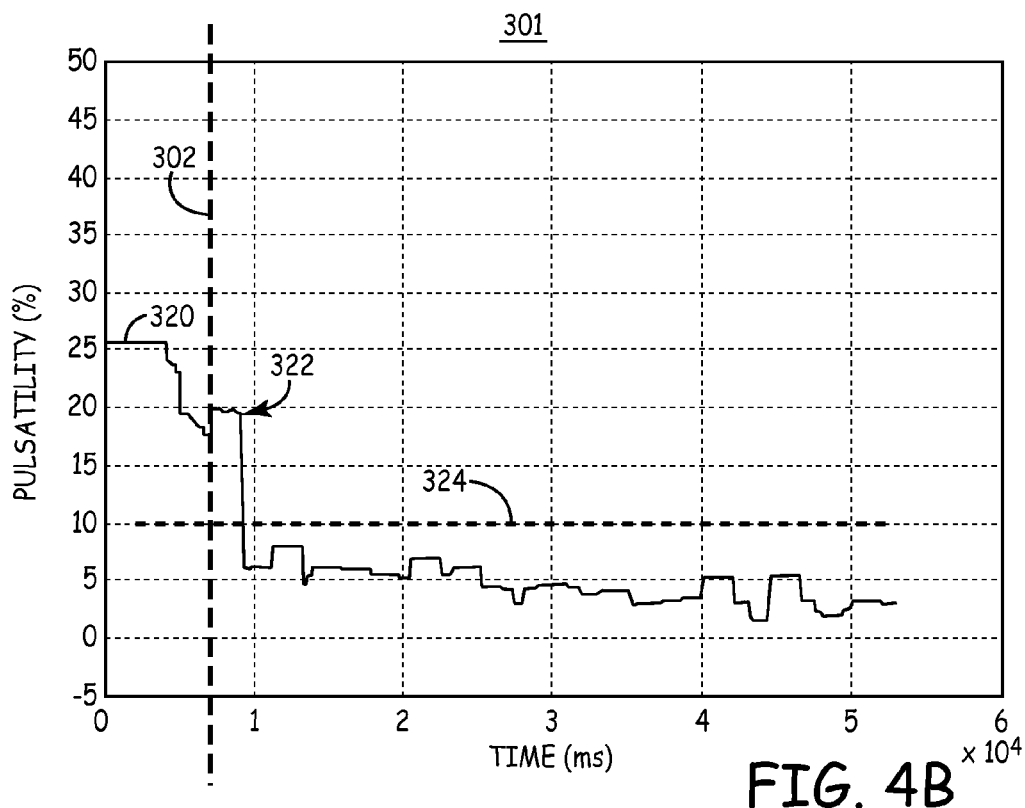
FIG. 4B is a time-based plot of a pulsatility percentage computed from the peak amplitude signal and the moving average signal of the voltage signal in FIG. 4A.

FIG. 4B is a time-based plot 301 of a pulsatility percentage computed from the peak amplitude signal 310 and the moving average signal 306. The ratio of the peak amplitude signal 310 to the moving average signal 306 is computed as a pulsatility metric and expressed as a percentage. Subsequent to fibrillation onset at 302, a sudden decrease 322 in the pulsatility percentage occurs. The sudden decrease 322 may slightly lag the actual onset of fibrillation at 302 due to the duration of the selected peak hold time window. Shorter windows may be used to detect the drop in pulsatility more quickly or multiple staggered peak hold time windows might be used to detect and hold sequential peak amplitudes used to update the pulsatility metric more frequently, effectively increasing the time resolution of the pulsatility metric.

In other embodiments, positive or negative maximum peak amplitudes may be detected from the voltage signal 304 and the absolute difference between the moving average 306 and the peak amplitude value may be computed as a pulsatility metric. The absolute difference may be expressed as a percentage of the moving average 306.

In plot 301, a pulsatility threshold 324 is shown to illustrate a threshold that may be used for confirming fibrillation and enabling delivery of a defibrillation shock. In this illustrative example, a threshold of 10% is shown, however other thresholds may be used. The threshold selected may be tailored to a given patient and may be an automatically adjusted threshold based on the moving average 306, a patient heart rate, or other physiological parameters.

A threshold applied to a pulsatility metric may include a time requirement. For example, the pulsatility percentage may be required to fall below the threshold 324 for at least a predefined interval of time, e.g. 2 seconds, before enabling shock delivery. As long as the pulsatility remains above the threshold, a shock may be withheld. If the pulsatility percentage briefly falls below the threshold 324 and then rises above the threshold again before the required time interval expires, the shock may continue to be withheld. A shock may be withheld indefinitely, up to some maximum period of time, or until the pulsatility metric remains below the threshold for the required time interval.

Figure 5:
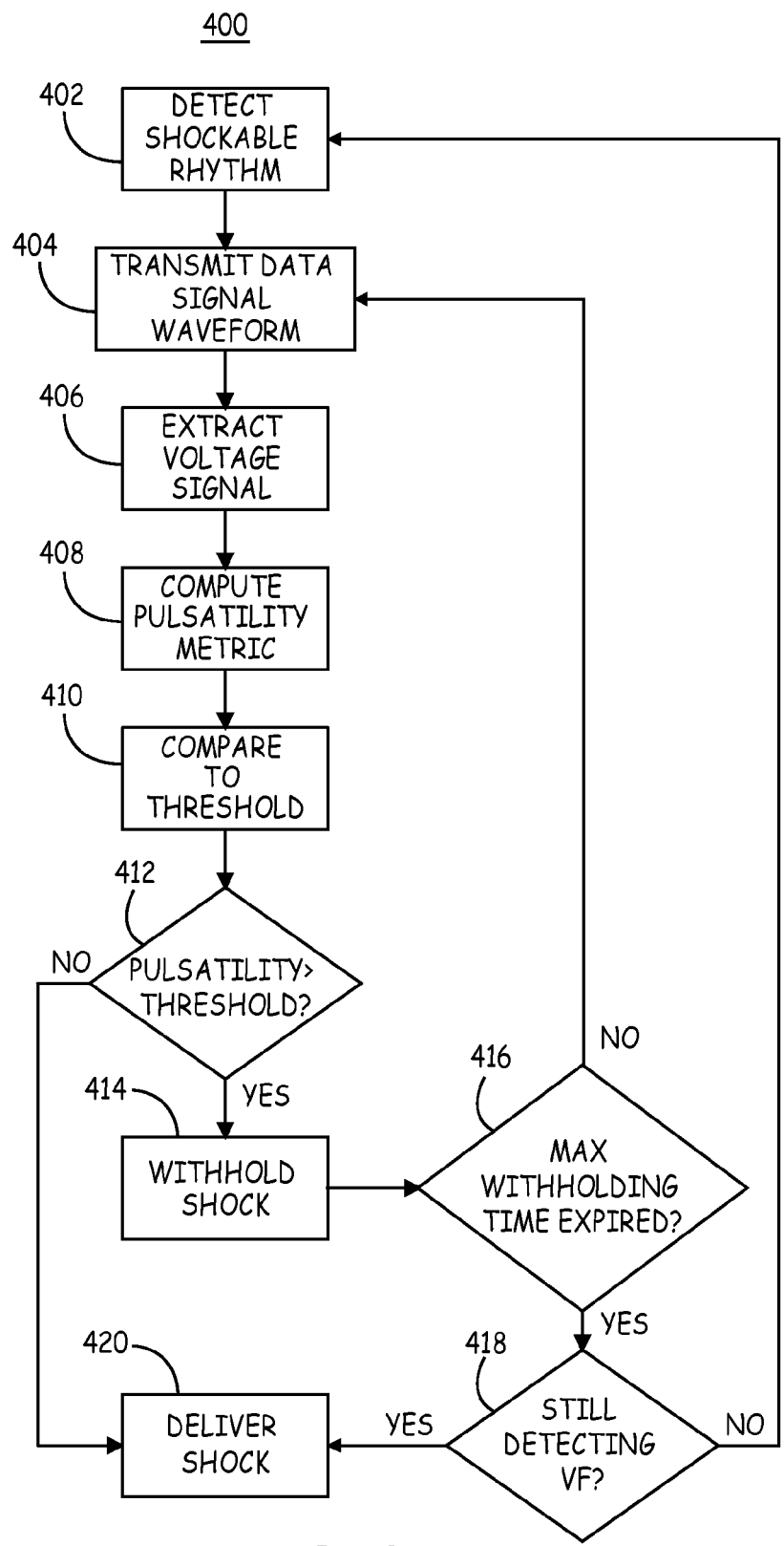
FIG. 5 is a flow chart of a method for reducing unnecessary defibrillation shocks in an ICD patient.

FIG. 5 is a flow chart 400 of a method for reducing unnecessary defibrillation shocks in an ICD patient. Flow chart 200 is intended to illustrate the functional operation of the device, and should not be construed as reflective of a specific form of software or hardware necessary to practice the methods described. It is believed that the particular form of software will be determined primarily by the particular system architecture employed in the device and by the particular detection and therapy delivery methodologies employed by the device. Providing software to accomplish the described functionality in the context of any modern IMD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 402, a shockable rhythm is detected by an ICD. The initial shockable rhythm detection may be based on EGM event intervals, EGM signal morphology analysis, other physiological signals, or any combination thereof.

A data signal waveform from a supporting device is transmitted at block 404. The data signal waveform may be a current signal injected for use in measuring transimpedance or may be a data signal waveform that includes other physiological data or information being transmitted from the supporting device to the ICD (or another device). The data signal may be transmitted in response to a request from the ICD upon detecting a shockable rhythm or may be continuously transmitted so that it is available for use as needed by the ICD.

At block 406, the voltage signal is measured by a dipole that is electrically coupled to the ICD, e.g. an electrode pair carried by the ICD housing and/or lead(s) coupled to the ICD, such that the ICD receives the voltage signal directly. Alternatively, the voltage signal is measured at a dipole of a second supporting device that then transmits the voltage signal, or processed pulsatility metric data, to the ICD. The second supporting device may or may not be electrically wired to the ICD for signal transmission. The voltage signal may be extracted from a data signal waveform that includes other physiological signal information obtained by the supporting device.

At block 408, a pulsatility metric is computed from the measured voltage signal as described above. The pulsatility metric is compared to a predefined detection threshold (or automatically adjusted threshold based on the moving average, heart rate or other parameter) at block 410. If the pulsatility metric is greater than the threshold, as determined at decision block 412, a shock therapy is withheld at block 414. A supra-threshold pulsatility metric indicates the heart is still beating effectively and the patient may be hemodynamically stable enough to avoid delivering a shock.

As described above, the threshold applied at block 410 may include a time requirement such that short fluctuations below the threshold that are less than the defined time requirement will still result in the shock being withheld. If the pulsatility metric falls below the threshold, for the required time interval, the shock is delivered at block 420.

If the shock is withheld, a timer may be started to limit the maximum duration that shock therapy is withheld when fibrillation is still being detected. At decision block 416, the control module determines if a maximum shock withholding time interval has expired. If not the ICD continues to monitor the pulsatility metric by returning to block 404. If the maximum shock withholding time is expired (block 416), and the ICD is still detecting VF, as determined at decision block 418, a shock therapy is delivered at block 420.

The transmission and measurement dipoles for monitoring transimpedance for use in reducing unnecessary ICD shocks may be positioned to include a portion of the heart therebetween to allow the pulsatility of the heart and myocardium to be monitored. Alternatively, the two distinct dipoles may be positioned at other body locations since pulsatility in other body tissues will also decline when the heart is in fibrillation.

Figure 6:
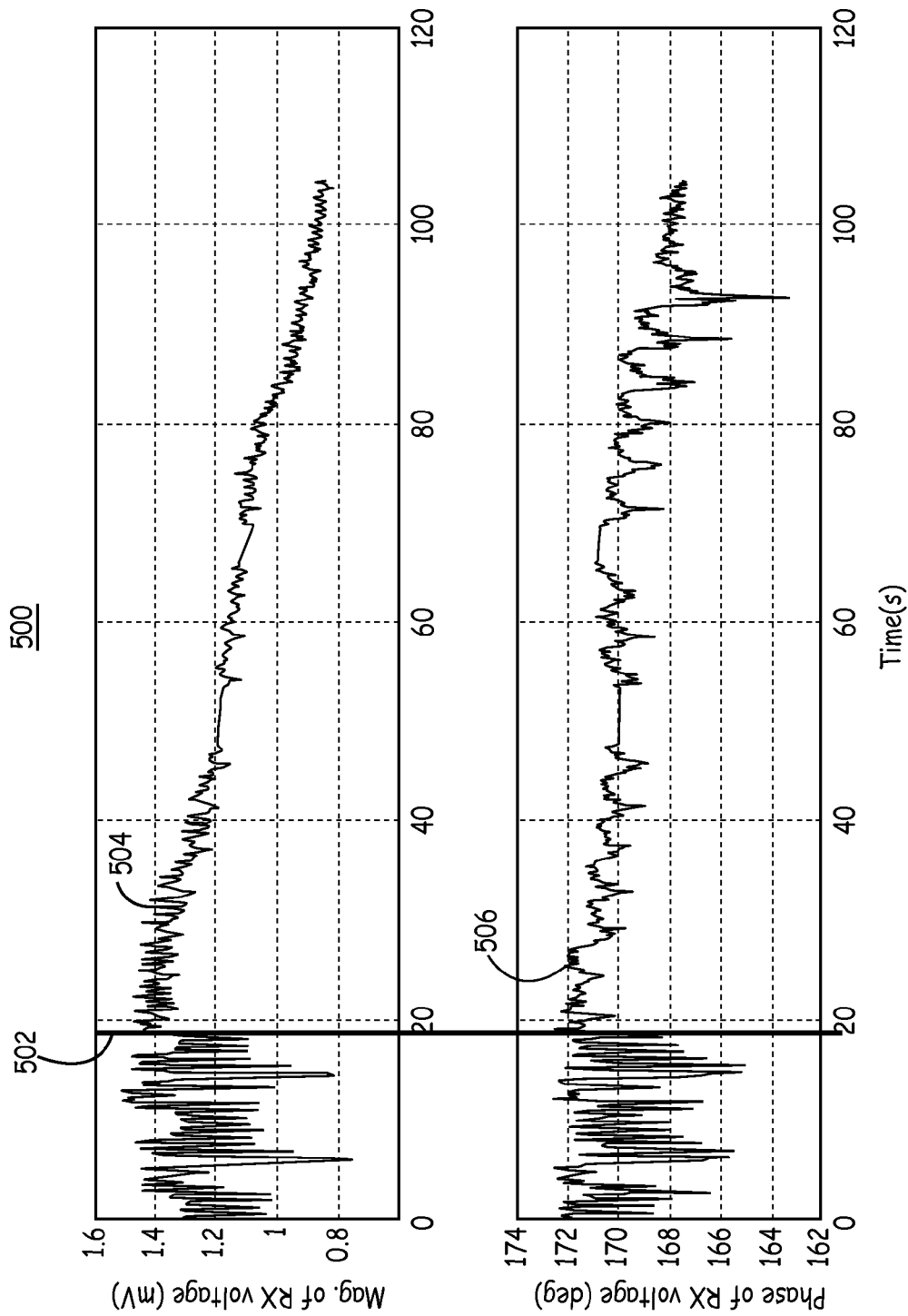
FIG. 6 is a time-based plot of a voltage signal measured using a dipole spaced apart from a transmission dipole via transimpedance for monitoring pulsatility of a volume of tissue based on changes in transimpedance.

FIG. 6 is a time-based plot 500 of a voltage signal measured using a measurement dipole spaced apart from a transmission dipole for monitoring pulsatility of a volume of tissue based on changes in transimpedance. In FIG. 6, the magnitude signal 504 of the measured voltage and the phase signal 506 of the measured voltage are plotted over time, before and after fibrillation is induced at 502 in an experimental subject. As can be seen in FIG. 6, the variation in the voltage magnitude 504 decreases significantly after fibrillation onset 502. The voltage magnitude signal 504 may therefore be used for computing a pulsatility metric has described above.

As also seen in FIG. 6, the variation in the phase of the voltage signal 506 also changes significantly after the onset of fibrillation at 502. As such, the phase change in the measured voltage signal caused by pulsatile impedance changes in body tissue may be used for determining a pulsatility metric in some embodiments. Because the relative decrease in phase change as a percentage of the peak-to-peak signal prior to fibrillation onset 502 is smaller than the change in the voltage magnitude, the use of the voltage phase may be less sensitive than the voltage magnitude. It is recognized, however, that either the voltage magnitude or phase, or a combination of both, may be used for computing a pulsatility metric. When the voltage phase is used, a similar signal processing method that utilizes a moving average and a peak amplitude of the voltage phase may be used for computing a pulsatility percentage.

Thus, a medical device system and method for monitoring cardiac or tissue pulsatility in a patient have been presented in the foregoing description with reference to specific embodiments. It is appreciated that various modifications to the referenced embodiments may be made without departing from the scope of the disclosure as set forth in the following claims.

The invention claimed is:

1. A method, comprising:
   delivering a non-stimulating electrical current using a first dipole located along a first body location and comprising a first electrode and a second electrode;
   measuring a voltage signal using a second dipole located at a second body location spaced apart from the first body location, the measured voltage signal corresponding to the electrical current being conducted through a portion of the patient's body, the second dipole comprising a third electrode and a fourth electrode different than the first electrode and the second electrode;
   computing a pulsatility metric in response to the measured voltage signal;
   detecting a physiological condition in response to the pulsatility metric; and
   sensing a physiological signal using a transducer at the first body location, wherein delivering the non-stimulating electrical current comprises wirelessly transmitting a data signal correlated to the physiological signal through the portion of the patient's body to a processor configured to receive the data signal.

2. The method of claim 1, further comprising comparing the pulsatility metric to a threshold and withholding a therapy in response to the pulsatility metric exceeding the threshold.

3. The method of claim 1, further comprising:
   sensing cardiac electrical signals using a pair of electrodes;
   detecting a tachycardia in response to the sensed cardiac electrical signals;
   computing the pulsatility metric in response to detecting the tachycardia;
   comparing the pulsatility metric to a threshold; and
   withholding a defibrillation shock in response to the pulsatility metric exceeding the threshold.

4. The method of claim 1, wherein the voltage signal comprises a magnitude and a phase and computing the pulsatility metric comprises determining a phase of the voltage signal.

5. The method of claim 1, further comprising:
   transmitting a wireless request signal from a first device carrying the second dipole to a second device carrying the first dipole, the request signal requesting the second device to transmit the non-stimulating electrical current;
   sending the current signal from the second device using the first dipole;
   measuring the voltage signal at the first device using the second dipole.

6. The method of claim 1, further comprising:
   deploying a first device carrying the first dipole at a first location;
   deploying a second device carrying the second dipole at a second location;
   the first and second devices being configured for wireless communication with each other.

7. The method of claim 1, wherein delivering the non-stimulating electrical current comprises:
   wirelessly transmitting a data communication signal from a first device carrying the first dipole to a second device carrying the second dipole;
   receiving the data communication signal at the second dipole; and
   extracting the voltage signal from the data communication signal.

8. The method of claim 7, further comprising:
   transmitting information corresponding to the non-stimulating electrical current in the data communication signal;
   computing a transimpedance signal in response to the information and the extracted voltage signal; and
   computing the pulsatility metric in response to the transimpedance signal.

9. A method, comprising:
   delivering a non-stimulating electrical current using a first dipole located along a first body location and comprising a first electrode and a second electrode;
   measuring a voltage signal using a second dipole located at a second body location spaced apart from the first body location, the measured voltage signal corresponding to the electrical current being conducted through a portion of the patient's body, the second dipole comprising a third electrode and a fourth electrode different than the first electrode and the second electrode;
   computing a pulsatility metric in response to the measured voltage signal; and detecting a physiological condition in response to the pulsatility metric, wherein computing a pulsatility metric comprises:
determining a peak amplitude using the measured voltage signal;
computing a moving average using the measured voltage signal; and
computing a ratio of the peak amplitude and the moving average.

10. An implantable medical device system, comprising:
a first dipole to deliver a non-stimulating electrical current, the first dipole comprising a first electrode and a second electrode adapted to be deployed along a first body location;
a second dipole to measure a voltage signal resulting from the non-stimulating electrical current being conducted through a portion of a patient's body; the second dipole comprising a third electrode and a fourth electrode different than the first electrode and the second electrode and adapted to be deployed along a second body location spaced apart from the first body location;
a processor configured to compute a pulsatility metric in response to the measured voltage signal and to detect a physiological condition in response to the pulsatility metric;
a transducer sensing a physiological signal at the first body location; and
a data transmission module configured to wirelessly transmit a data signal correlated to the physiological signal through the portion of the patient's body via the first dipole, wherein the processor is configured to extract the measured voltage at the second dipole from the data signal.

11. The system of claim 10, further comprising a therapy delivery module,
wherein the processor is further configured to compare the pulsatility metric to a threshold and withhold a therapy to be delivered by the therapy delivery module in response to the pulsatility metric exceeding the threshold.

12. The system of claim 10, further comprising:
a pair of electrodes to sense cardiac electrical signals; and
an event detector to detect a tachycardia in response to the sensed cardiac electrical signals, wherein the processor is configured to compute the pulsatility metric in response to detecting the tachycardia, compare the pulsatility metric to a threshold, and withhold a defibrillation shock in response to the pulsatility metric exceeding the threshold.

13. The system of claim 10, wherein the voltage signal comprises a magnitude and a phase and computing the pulsatility metric comprises determining a phase of the voltage signal.

14. The system of claim 10, further comprising:
a first device carrying the first dipole and comprising a first telemetry module to transmit a wireless request signal requesting the non-stimulating electrical current; and
a second device carrying the second dipole and comprising a second telemetry module for receiving the request signal and for transmitting the non-stimulating electrical current in response to the request signal.

15. The system of claim 10, further comprising:
a first device carrying the first dipole; and
a second device carrying the second dipole, the first and second devices being configured for wireless communication with each other.

16. The system of claim 10, further comprising:
a first device comprising a first telemetry module and carrying the first dipole, the first device configured to wirelessly transmit a data communication signal using the first dipole; and
a second device comprising a second telemetry module and carrying the second dipole, the second device configure to receive the data communication signal using the second dipole, wherein the processor is configured to extract the voltage signal from the data communication signal.

17. The system of claim 16 wherein the first device is further configured to transmit information corresponding to the non-stimulating electrical current in the data communication signal;
the processor further configured to compute a transimpedance signal in response to the information and the extracted voltage signal, and compute the pulsatility metric in response to the transimpedance signal.

18. An implantable medical device system, comprising:
a first dipole to deliver a non-stimulating electrical current, the first dipole comprising a first electrode and a second electrode adapted to be deployed along a first body location;
a second dipole to measure a voltage signal resulting from the non-stimulating electrical current being conducted through a portion of a patient's body; the second dipole comprising a third electrode and a fourth electrode different than the first electrode and the second electrode and adapted to be deployed along a second body location spaced apart from the first body location; and
a processor configured to compute a pulsatility metric in response to the measured voltage signal and to detect a physiological condition in response to the pulsatility metric, wherein computing the pulsatility metric comprises:
determining a peak amplitude using the measured voltage signal;
computing a moving average using the measured voltage signal; and
computing a ratio of the peak amplitude and the moving average.

19. A computer-readable medium storing a set of instructions which cause a processor of a medical device system to:
control the delivery of a non-stimulating electrical current using a first dipole located along a first body location and comprising a first electrode and a second electrode;
measure a voltage signal using a second dipole located at a second body location spaced apart from the first body location, the voltage corresponding to the electrical current being conducted through a portion of the patient's body, the second dipole comprising a third electrode and a fourth electrode different than the first electrode and the second electrode;
compute a pulsatility metric in response to the measured voltage;
detect a physiological condition in response to the pulsatility metric; and
sensing a physiological signal using a transducer at the first body location, wherein delivering the non-stimulating electrical current comprises wirelessly transmitting a data signal correlated to the physiological signal through the portion of the patient's body to a processor configured to receive the data signal.

* * * * *